United States Patent [19]

Lange et al.

[11] Patent Number: 5,281,595
[45] Date of Patent: Jan. 25, 1994

[54] ALKYLENEDIOXYPHENYL ETHER DERIVATIVES HAVING ANTI-ISCHAEMIC, MEMORY ENHANCING AND ANTI-CONVULSIVE ACTIVITY

[75] Inventors: Josephus H. M. Lange; Gerrit P. Toorop; Ineke v. Wijngaarden; Jacobus A. J. den Hartog, all of Weesp, Netherlands

[73] Assignee: Duphar International Research B.V., Weesp, Netherlands

[21] Appl. No.: 852,962

[22] Filed: Mar. 17, 1992

[30] Foreign Application Priority Data

Mar. 20, 1991 [EP] European Pat. Off. .......... 91200618

[51] Int. Cl.$^5$ ................ A61K 31/495; A61K 31/445; C07D 405/04; C07D 405/06
[52] U.S. Cl. ................................. 514/253; 514/254; 514/255; 514/317; 514/321; 514/327; 544/377; 544/398; 544/401; 546/197; 546/217; 546/236
[58] Field of Search .......... 544/398, 401, 377; 546/197, 217, 236; 514/253, 255, 321, 254, 317, 327

[56] References Cited

U.S. PATENT DOCUMENTS

| | | | |
|---|---|---|---|
| 3,996,279 | 12/1976 | Schlager | 544/398 |
| 4,100,285 | 7/1978 | Murai et al. | 544/398 |
| 4,535,159 | 8/1985 | Forné et al. | 546/197 |
| 4,574,156 | 3/1986 | Morita et al. | 544/398 |

FOREIGN PATENT DOCUMENTS

| | | |
|---|---|---|
| 0159566 | 10/1985 | European Pat. Off. . |
| 0404694 | 12/1990 | European Pat. Off. . |
| 418430 | 3/1991 | European Pat. Off. . |
| 453365 | 10/1991 | European Pat. Off. ......... 544/398 |

OTHER PUBLICATIONS

Patents Abstracts of Japan, vol. 14, No. 208 (C-714) (4151) Apr. 27, 1990 & JP-A-245464 (Mejji Seika Kaisha Ltd.).
Chemical & Pharmaceutical Bulletin, vol. 35, No. 8, Aug. 1987 pp. 3270-3275; JP; H. Ohtaka et al, "Benzylpiperazine Deriva . . . ".
Chemical & Pharmaceutical Bulletin, vol. 35, No. 7, Jul. 1987 pp. 2774-2781; JP; H. Ohtaka et al, "Benzylpiperazine Deriv . . . ".
Chemical & Pharmaceutical Bulletin, vol. 35, No. 7, Jul. 1987 pp. 2782-2791; JP; H. Ohtaka et al, "Benzylpiperazine Deriv . . . ".

*Primary Examiner*—Cecilia Tsang
*Attorney, Agent, or Firm*—Stevens, Davis, Miller & Mosher

[57] ABSTRACT

The invention relates to compounds having anti-ischaemic activity, memory enhancing activity and anti-convulsive activity of the formulae 1A and 1B

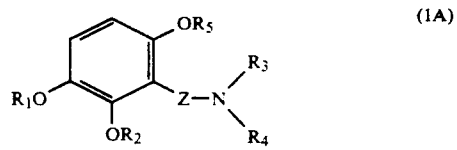 (1A)

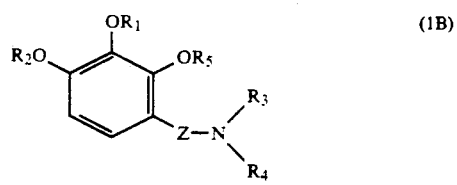

(1B)

wherein $R_1+R_2$ together form an alkylene group having 1-3 C-atoms which may be substituted with one or more alkyl group(s) having 1-3 C-atoms and the remaining R and Z variables are defined as disclosed herein, or a pharmacologically acceptable salt thereof.

6 Claims, No Drawings

ALKYLENEDIOXYPHENYL ETHER DERIVATIVES HAVING ANTI-ISCHAEMIC, MEMORY ENHANCING AND ANTI-CONVULSIVE ACTIVITY

The invention relates to a group of new alkylenedioxyphenyl ether derivatives having interesting anti-ischaemic activity, memory enhancing activity and anti-convulsive activity, to a method of preparing said compounds, and to pharmaceutical compositions comprising at least one of these compounds as the active component. There is an increasing clinical interest in an effective pharmalogical symptomatic treatment for cerebral and peripheral ischaemic diseases. In patients suffering from these diseases the impaired blood supply causes an inadequate delivery of oxygen and other nutrients to the tissue as well as a diminished removal of metabolic waste products resulting in structural injury and functional deterioration. Anti-convulsive compounds can be useful in the treatment of epilepsy.

The object of the present invention is to provide active compounds with anti-ischaemic, memory enhancing and anti-convulsive properties.

It has been found surprisingly that compounds of formulae 1A and 1B

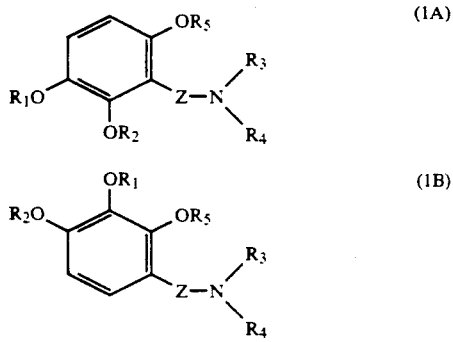

wherein
- $R_1 + R_2$ together form an alkylene group having 1–3 C-atoms which may be substituted with one or more alkyl group(s) having 1–3 C-atoms;
- Z is methylene optionally substituted with one alkyl group having 1–3 C-atoms, or with one phenylalkyl group with 1–3 C-atoms in the alkyl group, which phenyl group may be substituted with a group $(R_6)_p$ wherein $R_6$ is halogen, hydroxy, alkyl or hydroxyalkyl having 1–5 C-atoms, alkoxy having 1–3 C-atoms, S-alkyl, S(O)-alkyl or S(O)$_2$-alkyl having 1–3 C-atoms, amino, mono- or dialkylamino having 1–3 C-atoms per alkyl group, trifluoromethyl, trifluoromethoxy, a sulphonylamido group $SO_2NHR$ or a carbalkoxy group $COOR$ wherein R is alkyl having 1–4 C-atoms, the group COOH, $SO_3H$, $CONH_2$, the amidino group or cyano group, and p has the value 0–3;
- $R_3$ and $R_4$ independent of each other represent hydrogen, alkyl having 1–10 C-atoms, alkenyl or alkynyl having 3–10 C-atoms, cycloalkyl having 3–8 C-atoms, cycloalkyl-alkyl having 3–8 ring atoms and 1–5 C-atoms in the alkyl group, phenylalkyl or heteroaryl-alkyl having 1–5 C-atoms in the alkyl group, phenylalkenyl, heteroaryl-alkenyl, phenylalkynyl or heteroaryl-alkynyl group having 3–5 C-atoms in the alkenyl group or alkynyl group, which groups $R_3$ and $R_4$ may be substituted with a group $(R_6)_p$ wherein $R_6$ and p have the above mentioned meanings, or wherein $R_3 + R_4$ together with the nitrogen atom form a saturated or unsaturated heterocyclic group of 5–7 ring atoms, which may contain a second hetero-atom from the group consisting of oxygen, sulphur and nitrogen, which ring may be substituted with a group $(R_6)_p$ wherein $R_6$ and p have the above mentioned meanings, or with phenylalkyl, heteroaryl-alkyl, phenylalkenyl, heteroaryl-alkenyl, phenylalkynyl or heteroaryl-alkynyl having at most 3 C-atoms in the alkyl, alkenyl or alkynyl part, which groups may be substituted with a group $(R_6)_p$ wherein $R_6$ and p have the above-mentioned meanings, or which ring may be annelated with a phenyl group;
- $R_5$ is alkyl having 1–12 C-atoms, alkenyl or alkynyl having 3–12 C-atoms, cycloalkyl having 3–8 C-atoms, cycloalkyl-alkyl having 3–8 ring atoms and 1–5 C-atoms in the alkyl group, phenylalkyl or heteroaryl-alkyl having 1–5 C-atoms in the alkyl sub-group, phenylalkenyl, heteroaryl-alkenyl, phenylalkynyl or heteroaryl-alkynyl having 3–5 C-atoms in the alkenyl sub-group or alkynyl sub-group, which groups may be substituted with a group $(R_6)_p$, wherein $R_6$ and p have the above-mentioned meanings, and which alkyl sub-groups, alkenyl sub-groups and alkynyl sub-groups may contain a group —O—, —S— or CO, prodrugs and pharmaceutically acceptable acid addition salts thereof have interesting and valuable anti-ischaemic, memory enhancing and anti-convulsive properties.

Prodrugs are derivatives of these compounds which as such are inactive, from which, after splitting off an easily removable group, for example an ester group or an ether group, an active compound of formula 1A or 1B is obtained. Suitable acids with which suitable addition salts can be formed are, for example, hydrochloric acid, sulphuric acid, phosphoric acid, nitric acid, and organic acids like citric acid, fumaric acid, maleic acid, tartaric acid, acetic acid, benzoic acid, p-toluene sulphonic acid, methane sulphonic acid, etc.

One or more centers of chirality may be present in the compounds having formula 1A or 1B. The invention relates both to racemates and the individual isomers of the compounds having formulae 1A and 1B.

The anti-ischaemic and memory enhancing activity of the compounds has been determined by means of the in vivo hypobaric hypoxia test, the in vitro cardiomyocytes test and the in vivo memory test. These tests were used to characterize substances with cerebro- and/or peripheral-protective activity.

The anti-convulsive activity of the compounds has been determined by means of chemically induced tonic convulsions in vivo.

1) Hypobaric activity in vivo

Cerebro-protective activity was determined by measuring the prolongation of the survival time of conscious mice under hypobaric conditions.

Groups of 3 overnight fasted male NMRI mice (15–20 g) are dosed ip (30 mg/kg), 30 minutes before being placed in a chamber at hypobaric pressure of 200 mBar. The prolongation of the survival time is expressed in percentage increase in respiration time, compared to that of the placebo treated control group.

2) Cardiomyocytes in vitro

Cyto-protective properties were determined in an in vitro model using isolated calcium tolerant cardiomyocytes according to L. Verdonck et al (Life Sciences, vol. 38, (1986) 765–772).

Cardiomyocytes were isolated from male Wistar rat hearts. Rod shaped cells were incubated with the compound to be tested for 30 min. Injury was induced by e.g. veratrine (100 μg/ml) or by hypoxia upon which the cells became rounded unless protected by the compound. After 20 min. the remaining rod-shaped cells were counted and the protecting efficacy of the compound was determined.

3) Memory testing under hypoxic conditions

Cerebroprotective activity was determined by studying the prevention of hypoxia induced amnesia in gerbils.

In groups of 6–8 gerbils step through passive avoidance was measured after exposure to hypoxia (4% $O_2$, 96% $N_2$) until gasping was observed. Memory testing was performed 4 hrs after drug administration and exposure to hypoxia.

4) Chemically induced tonic convulsions in vivo

Protection against pentylene-tetrazole-induced convulsions (50 mg/kg i.v.) was demonstrated in male NMRI-mice, weighing 18–24 g.

Tonic convulsions were measured 60 minutes after oral administration of the test compound. Suppression of the tonic extensor phase was considered to be the criterion for the anti-convulsive effect. (Purpura D. P., Penry J. K., Tower D. B., Woodburry D. M., Walters R. D. (eds.), Experimental models of epilepsy, Raven Press, New York (1972)).

The compounds having formulae 1A and 1B, wherein the symbols have the above-mentioned meaning are new compounds which can be prepared according to methods known per se.

For example compounds having formula 1A can be obtained by first preparing a compound having formula 2

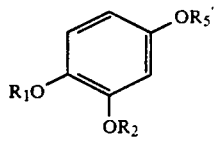

(2)

wherein $R_1$ and $R_2$ have the above mentioned meaning and wherein $R'_5$ is a so-called directed ortho-metallating group (see for example Acc. Chem. Res., 15, 306 (1982)), such as —CH$_2$OCH$_3$(MOM), —CH(CH$_3$)OC$_2$H$_5$, —CH$_2$O(CH$_2$)$_2$Si(CH$_3$)$_3$(SEM) and the like, via known procedures (see for example, "Protective Groups in Organic Chemistry", Ed. J. F. W. McOmie, Plenum Press, London (1973), Chapter 4; Synthesis, 276 (1975); Synthesis 244 (1976); J. Org. Chem., 44, 2480 (1979)), from the corresponding phenolic compounds 2 wherein $R'_5$ is hydrogen. The so-obtained compounds of formula 2 can be converted into the corresponding compounds of formula 3

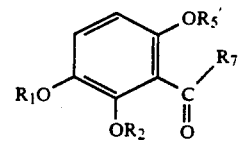

(3)

wherein $R_7$ is hydrogen, alkyl having 1–3 C-atoms, phenylalkyl with 1–3 C-atoms in the alkyl group, which phenyl group may be substituted with a group $(R_6)_p$ wherein $R_6$ and p have the above mentioned meanings, via regioselective deprotonation with a strong base, for example n-butyllithium and the like, followed by reaction with an electrophile $R_7$—CO—X, wherein X represents a leaving group, for example halogen (see for analogous ortho-directed metallations for example J. Org. Chem., 53, 3936 (1988); J. Heterocyclic Chem., 26, 1827 (1989)).

The so-obtained compounds of formula 3 can be converted into the corresponding compounds of formula 4

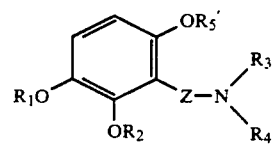

(4)

by a reductive amination reaction with an amine of the formula $R_3R_4NH$, in which formulae $R_1$–$R_4$ and Z have the meanings given in formula 1A, and $R'_5$ and $R_7$ have the meanings given above. This reductive amination reaction can be carried out with a suitable reducing agent such as NaCNBH$_3$ in an inert solvent, for example acetonitrile, or by other reductive amination methods (see for example Russ. Chem. Rev., 49, 14 (1980), or Synthesis, 135 (1975)). In some cases the addition of an acid catalyst may be desirable to enhance the reaction rate.

The so-obtained compounds of formula 4 can be converted into the corresponding compounds of formula 5

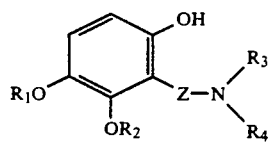

(5)

in which formula $R_1$–$R_4$ and Z have the meanings given in formula 1A, by means of an acid-catalyzed removal of $R'_5$.

The so-obtained compounds of formula 5 can be converted into the corresponding compounds of formula 1A wherein $R_5$ has the above mentioned meanings by means of a reaction with a compound of the formula $R_5$—X, wherein X is a so-called leaving group. This reaction is preferably carried out in an inert solvent such as dimethylsulphoxide (DMSO), N,N-dimethylformamide (DMF) and the like, in the presence of a suitable base such as sodium hydride or potassium tert-butoxide and the like. Sometimes the addition of sodium iodide is desirable. The reaction may be carried out at somewhat elevated temperatures.

Compounds having general formula 1B can be obtained for example by first preparing a compound having formula 6

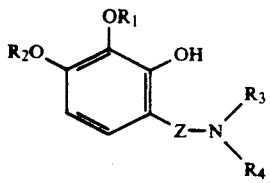

wherein $R_1$–$R_4$ and Z have the above mentioned meanings, by reacting a compound of the formula 7

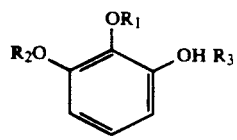

with a compound of the formula $R_3R_4NH$ and an aldehyde of the formula $R_7CHO$, in which formulae $R_1$–$R_4$ and $R_7$ have the above mentioned meaning. This so-called Mannich-reaction is preferably carried out in an inert organic solvent, such as ethanol or acetonitrile.

The starting compounds of formula 7 are known or can be obtained analogously to known compounds (see for example W. Baker and R. I. Savage, J. Chem. Soc., 1602 (1938)).

The so-obtained compounds of formula 6 can be converted into the corresponding compounds of formula 1B wherein $R_5$ has the above mentioned meanings in the same manner as described above for the preparation of compounds having formula 1A from compounds having formula 5.

EXAMPLE 1 a) 5-(1-ethoxyethoxy)-1,3-benzodioxole

A stirred solution of 3,4-methylenedioxyphenol (6.0 g, 43.5 mmol), ethyl vinyl ether (3.75 g, 52.0 mmol) and a catalytic amount of trichloroacetic acid (50 mg, 0.3 mmol) in chloroform (50 ml) was stirred for two hours at room temperature. Aqueous NaOH (2N, 50 ml) was added and the resulting mixture was extracted with diethyl ether (3 times). The combined ether extracts were washed with aqueous NaOH (2N) and water, respectively, dried over $Na_2SO_4$, filtered and evaporated in vacuo to yield 5-(1-ethoxyethoxy)-1,3-benzodioxole (8.96 g, 98% yield; compound No. 1) as an oil.

b) 5-(1-ethoxyethoxy)-4-formyl-1,3-benzodioxole n-Butyllithium (18.6 ml of a 2.5M solution in hexane, 46.5 mmol) and N,N,N',N'-tetramethylethylenediamine (5.38 g, 46.3 mmol), respectively, were added (using a syringe) to a stirred solution of 5-(1-ethoxyethoxy)-1,3-benzodioxole (8.9 g, 42.4 mmol) in dry THF (100 ml) in a nitrogen atmosphere at −78° C. The resulting solution was allowed to attain room temperature and then cooled to −78° C. A solution of N,N-dimethylformamide (3.70 g, 50.6 mmol) in dry THF (20 ml) was added using a syringe, and the reaction mixture was allowed to attain room temperature. The resulting mixture was quenched with water and extracted with diethyl ether (3 times). The combined ether layers were washed with water (2 times), dried over $Na_2SO_4$, filtered and evaporated in vacuo to to yield 5-(1-ethoxyethoxy)-4-formyl-1,3-benzodioxole (9.7 g, 96% yield; compound No. 2) as a pale yellow solid, m.p. 48°–50° C.

In a similar manner 5-methoxymethoxy-1,3-benzodioxole was converted into 4-formyl-5-methoxymethoxy-1,3-benzodioxole (compound No. 3), melting point 84°–86° C.

c) 5-(1-ethoxyethoxy)-4-(4-methylpiperazinylmethyl)-1,3-benzodioxole $NaCNBH_3$ (6.4 g, 101.8 mmol) was added to a stirred solution of 5-(1-ethoxyethoxy)-4-formyl-1,3-benzodioxole (16.0 g, 67.2 mmol) and 1-methylpiperazine (20.2 g, 201.7 mmol) in $CH_3CN$ (150 ml). Acetic acid (10 ml) was added dropwise to the solution in one hour at room temperature, to keep the pH neutral (pH=7). After 3 hours of additional stirring, most of the $CH_3CN$ was evaporated in vacuo. Aqueous NaOH (2N, 300 ml) was added and the resulting mixture was extracted with diethyl ether (3 times). The combined ether extracts were washed with an aqueous solution of $Na_2CO_3$, dried over $Na_2SO_4$, filtered and evaporated to yield 26 g of a crude oil. This oil was purified by flash chromatography (eluent gradient; dichloromethane/methanol/25% aqueous ammonia=95/4.5/0.5 to 85/14/1 (v/v) to give 5-(1-ethoxyethoxy)-4-(4-methylpiperazinylmethyl)-1,3-benzodioxole (16.0 g, 74% yield, compound No. 4) as a colorless oil.

In a similar manner the compounds of formula 4, wherein the $R_1$–$R'_5$ and Z have the meanings indicated in Table A were prepared.

TABLE A

| Comp. no. | $R_1 + R_2$ | $R_3 (+) R_4$ | $R'_5$ | Z | m.p. (°C.) |
|---|---|---|---|---|---|
| 5 | —$CH_2$— | —$(CH_2)_5$— | —$CH(CH_3)OC_2H_5$ | —$CH_2$— | oil |
| 6 | —$CH_2$— | —$(CH_2)_2N((CH_2)_2CH_3)(CH_2)_2$— | —($CH(CH_3)OC_2H_5$ | —$CH_2$— | oil |
| 7 | —$CH_2$— | $C_2H_5$ $C_2H_5$ | —$CH_2OCH_3$ | —$CH_2$— | oil | d) 5-hydroxy-4-(4-methylpiperazinylmethyl)-1,3-benzodioxole

Aqueous HCl (300 ml, 0.5N) was added to a stirred solution of 5-(1-ethoxyethoxy)-4-(4-methylpiperazinylmethyl)-1,3-benzodioxole (16.0 g, 49.7 mmol) in 2-propanol (300 ml) at room temperature, and stirring was continued for 15 minutes. The solution was extracted with diethyl ether, the aqueous layer was neutralised (pH=7) by adding aqueous NaOH(2N), and the water layer was evaporated in vacuo. The residue was extracted with diethyl ether (3 times). The combined organic layers were dried over $Na_2SO_4$, filtered and evaporated in vacuo to yield a crude oil (9.6 g). This oil was purified by flash chromatography (eluent: acetone/ethyl acetate=1/1 (v/v)) to yield 5-hydroxy-4-(4-methylpiperazinylmethyl)-1,3-benzodioxole (7.6 g, 61% yield, compound No. 8) as a solid, m.p. 85°–87° C.

In a similar manner the compounds of formula 5 wherein $R_1$–$R_4$ and Z have the meanings indicated in Table B were prepared.

TABLE B

| Comp. no. | $R_1 + R_2$ | $R_3 (+) R_4$ | Z | m.p. (°C.) |
|---|---|---|---|---|
| 9 | —CH$_2$— | C$_2$H$_5$  C$_2$H$_5$ | —CH$_2$— | oil |
| 10 | —CH$_2$— | —(CH$_2$)$_5$— | —CH$_2$— | oil |
| 11 | —CH$_2$— | —(CH$_2$)$_2$N((CH$_2$)$_2$CH$_3$)(CH$_2$)$_2$— | —CH$_2$— | 190 | e)
4-(4-methylpiperazinylmethyl)-5-phenylpropoxy-1,3-benzodioxole .2HCl)

3-Phenylpropyl bromide (1.81 g, 9.1 mmol) was added to a mixture of 5-hydroxy-4-(4-methylpiperazinylmethyl)-1,3-benzodioxole (1.9 g, 7.6 mmol), sodium iodide (0.1 g, 0.7 mmol) and potassium tert-butoxide (1.12 g, 9.9 mmol) in DMSO (30 ml). The stirred mixture was heated at 80° C. for two hours. Thereafter, the mixture was allowed to attain room temperature, water was added and the resulting solution was extracted with diethyl ether (3 times), the combined ether extracts were washed with 2N aqueous NaOH and water respectively, and dried over Na$_2$SO$_4$. Gaseous HCl was added and the formed precipitate was filtered. This precipitate was recrystallised from 2-propanol/methanol=9/1 (v/v) to yield 4-(4-methylpiperazinylmethyl)-5-phenylpropoxy-1,3-benzodioxole. 2HCl (2.9 g, 87% yield; compound No. 12) as a white solid, m.p. 223°-225° C.

In a similar manner the compounds of formula 1A, wherein R$_1$-R$_5$ and Z have the meanings indicated in Table C were prepared.

In a similar manner the compounds of formula 6 wherein Z and R$_1$-R$_4$ have the meanings indicated in Table D were prepared.

TABLE D

| Comp. no. | $R_2 + R_2$ | $R_3 (+) R_4$ | Z | m.p. (°C.) |
|---|---|---|---|---|
| 26 | —CH$_2$— | C$_2$H$_5$  C$_2$H$_5$ | —CH$_2$— | oil |
| 27 | —CH$_2$— | —(CH$_2$)$_5$— | —CH$_2$— | 156-8 |
| 28 | —CH$_2$— | —(CH$_2$)$_2$N(CH$_3$)(CH$_2$)$_2$— | —CH$_2$— | 118-20 | b)
4-butoxy-5-(4-propylpierazinylmethyl)-1,3-benzodioxole .2HCl

Butyl bromide (1.71 g, 12.5 mmol) was added to a mixture of 5-(4-propylpiperazinylmethyl)-4-hydroxy-1,3-benzodioxole (2.9 g, 10.4 mmol), sodium iodide (0.1 g, 0.7 mmol) and potassium tert-butoxide (1.53 g, 13.5 mmol) in DMSO (30 ml). The stirred mixture was heated at 80° C. for 2 hours. Thereafter, the mixture was allowed to attain room temperature, water was added and the resulting solution was extracted with diethyl ether (3 times). The combined ether extracts were

TABLE C

| Comp. no. | $R_1 + R_2$ | $R_3 (+) R_4$ | $R_5$ | Z | salt | m.p. (°C.) |
|---|---|---|---|---|---|---|
| 13 | —CH$_2$— | C$_2$H$_5$  C$_2$H$_5$ | n-C$_5$H$_{11}$ | —CH$_2$— | HBr | 130-2 |
| 14 | —CH$_2$— | C$_2$H$_5$  C$_2$H$_5$ | (CH$_2$)$_3$C$_6$H$_5$ | —CH$_2$— | HBr | 145-7 |
| 15 | —CH$_2$— | —(CH$_2$)$_5$— | n-C$_3$H$_7$ | —CH$_2$— | HCl | 134-6 |
| 16 | —CH$_2$— | —(CH$_2$)$_5$— | n-C$_5$H$_{11}$ | —CH$_2$— | HCl | 142-4 |
| 17 | —CH$_2$— | —(CH$_2$)$_5$— | CH$_2$C$_6$H$_5$ | —CH$_2$— | free base | 100-2 |
| 18 | —CH$_2$— | —(CH$_2$)$_5$— | (CH$_2$)$_3$C$_6$H$_5$ | —CH$_2$— | HBr | 129-33 |
| 19 | —CH$_2$— | —(CH$_2$)$_2$N(CH$_3$)(CH$_2$)$_2$— | n-C$_4$H$_9$ | —CH$_2$— | 2HCl | 208 dec |
| 20 | —CH$_2$— | —(CH$_2$)$_2$N(CH$_3$)(CH$_2$)$_2$— | CH$_2$C$_6$H$_5$ | —CH$_2$— | 2HCl | 100-5 dec |
| 21 | —CH$_2$— | —(CH$_2$)$_2$N(CH$_3$)(CH$_2$)$_2$— | CH$_2$-2-Cl—C$_6$H$_4$ | —CH$_2$— | 2HCl | 172-5 |
| 22 | —CH$_2$— | —(CH$_2$)$_2$N((CH$_2$)$_2$CH$_3$)(CH$_2$)$_2$— | n-C$_4$H$_9$ | —CH$_2$— | 2HCl | 210-12 |
| 23 | —CH$_2$— | —(CH$_2$)$_2$N((CH$_2$)$_2$CH$_3$)(CH$_2$)$_2$— | CH$_2$C$_6$H$_5$ | —CH$_2$— | 2HCl | 219-21 |
| 24 | —(CH$_2$)$_2$— | —(CH$_2$)$_2$N(CH$_3$)(CH$_2$)$_2$— | (CH$_2$)$_3$C$_6$H$_5$ | —CH$_2$— | 2HCl | 198-201 |

EXAMPLE II a)
4-hydroxy-5-(4-propylpiperazinylmethyl)-1,3-benzodioxole

Aqueous formaldehyde (37%; 3.67 g, 45.3 mmol) was added dropwise to a stirred solution of 4-hydroxy-1,3-benzodioxole (5.2 g, 37.8 mmol) and N-propylpiperazine (5.8 g, 45.3 mmol) in acetonitrile (25 ml). The reaction mixture was stirred at room temperature for one hour and evaporated in vacuo. The remaining oil (13.0 g) was purified chromatographically (with ethylacetate/methanol=9/1 (v/v) as an eluent to give 4-hydroxy-5-(4-propylpiperazinylmethyl)-1,3-benzodioxole (5.9 g, 56% yield; compound No. 25), m.p. 115°-117° C.

washed with 2N aqueous NaOH and water, respectively. The combined ether extracts were extracted twice with HCl (10 ml of a 10% aqueous solution). The combined aqueous layers were extracted with diethyl ether and made alkaline (pH=13) by addition of NaOH (25 ml of a 50% aqueous solution).

The resulting solution was extracted twice with diethyl ether. The combined ether extracts were dried over Na$_2$SO$_4$ and filtered. The filtrate was saturated with gaseous hydrogen chloride and evaporated in vacuo to yield 4-butoxy-5-(4-propylpiperazinylmethyl)-1,3-benzodioxole.2HCl (2.04 g, 48% yield; compound no. 29) as a pure white solid, m.p. 245° C. (decomposition). In a similar manner the compounds of formula 1B wherein R$_1$-R$_5$ and Z have the meanings indicated in Table E were prepared.

TABLE E

| Comp. no. | $R_1 + R_2$ | $R_3 (+) R_4$ | $R_5$ | Z | salt | m.p. (°C.) |
|---|---|---|---|---|---|---|
| 30 | —CH$_2$— | C$_2$H$_5$  C$_2$H$_5$ | n-C$_5$H$_{11}$ | —CH$_2$— | HCl | 103-5 |
| 31 | —CH$_2$— | C$_2$H$_5$  C$_2$H$_5$ | (CH$_2$)$_3$C$_6$H$_5$ | —CH$_2$— | HCl | 116-8 |
| 32 | —CH$_2$— | —(CH$_2$)$_5$— | n-C$_5$H$_{11}$ | —CH$_2$— | HCl | 168-70 |
| 33 | —CH$_2$— | —(CH$_2$)$_5$— | CH$_2$C$_6$H$_5$ | —CH$_2$— | HCl | 205-8 |
| 34 | —CH$_2$— | —(CH$_2$)$_2$N(CH$_3$)(CH$_2$)$_2$— | n-C$_4$H$_9$ | —CH$_2$— | 2HCl | 198-201 |
| 35 | —CH$_2$— | —(CH$_2$)$_2$N(CH$_3$)(CH$_2$)$_2$— | CH$_2$C$_6$H$_5$ | —CH$_2$— | 2HCl | 262 dec. |
| 36 | —CH$_2$— | —(CH$_2$)$_2$N(CH$_3$)(CH$_2$)$_2$— | CH$_2$-2-Cl—C$_6$H$_4$ | —CH$_2$— | 2HCl | 257 dec. |
| 37 | —CH$_2$— | —(CH$_2$)$_2$N(CH$_3$)(CH$_2$)$_2$— | (CH$_2$)$_3$C$_6$H$_5$ | —CH$_2$— | 2HCl | 247 dec. |
| 38 | —CH$_2$— | —(CH$_2$)$_2$N((CH$_2$)$_2$CH$_3$)(CH$_2$)$_2$— | CH$_2$C$_6$H$_5$ | —CH$_2$— | 2HCl | 242 dec. |

We claim:

1. A compound of formula 1A or 1B

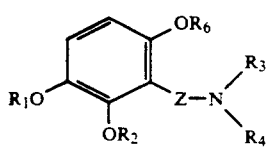
(1A)

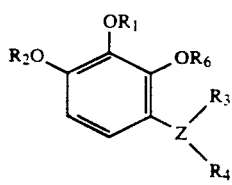
(1B)

wherein:

$R_1 + R_2$ together form an alkylene group having 1-3 C-atoms which may be substituted with one or more alkyl group(s) having 1-3 C-atoms;

Z is methylene optionally substituted with one alkyl group having 1-3 C-atoms, or with one phenylalkyl group with 1-3 C-atoms in the alkyl group, which phenyl group may be substituted with a group $(R_6)_p$ wherein $R_6$ is halogen, hydroxy, alkyl or hydroxyalkyl having 1-5 C-atoms, alkoxy having 1-3 C-atoms, S-alkyl, S(O)-alkyl or S(O)$_2$-alkyl having 1-3 C-atoms, amino, mono- or dialkylamino having 1-3 C-atoms per alkyl group, trifluoromethyl, trifluoromethoxy, a sulphonylamido group SO$_2$NHR or a carbalkoxy group COOR wherein R is alkyl having 1-4 C-atoms, the group COOH, SO$_3$H, CONH$_2$, the amidino group or cyano group, and p has the value 0-3;

$R_3$ and $R_4$ independent of each other represent hydrogen, alkyl having 1-10 C-atoms, alkenyl or alkynyl having 3-10 C-atoms, cycloalkyl having 3-8 C-atoms or cycloalkyl-alkyl having 3-8 atoms in the ring and 1-5 C-atoms in the alkyl group, or $R_3 + R_4$ together with the nitrogen atom form a piperidinyl or piperazinyl which may be substituted with 1-3 substituents selected from the group consisting of halogen, hydroxy and alkyl having 1-3 C atoms;

$R_5$ is alkyl having 1-12 C-atoms, alkenyl or alkynyl having 3-12 C-atoms, cycloalkyl having 3-8 C-atoms, cycloalkyl-alkyl having 3-8 ring atoms and 1-5 C-atoms in the alkyl group, phenylalkyl having 1-5 C-atoms in the alkyl sub-group, phenylalkenyl, or phenylalkynyl having 3-5 C-atoms in the alkenyl sub-group or alkynyl sub-group, which groups may be substituted with a group $(R_6)_p$, wherein $R_6$ and p have the above-mentioned meanings, and which alkyl sub-groups, alkenyl sub-groups and alkynyl sub-groups may contain a group —O—, —S— or CO, or a pharmaceutically acceptable salt thereof.

2. A composition having anti-ischaemic, memory enhancing and anti-convulsive activity which comprises an anti-ischaemically, memory enhancingly and anti-convulsively effective amount of at least one compound as claimed in claim 1 as active component and a pharmaceutically acceptable carrier.

3. A method of treating ischaemia, impaired memory or epilepsy, comprising administering a compound according to claim 1 to a patient suffering from at least one of these diseases.

4. A compound of formula 1A or 1B

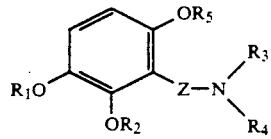
(1A)

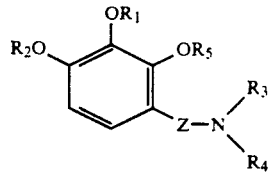
(1B)

wherein:

$R_1 + R_2$ together form an alkylene group having 1-3 C-atoms which may be substituted with one or more alkyl group(s) having 1-3 C-atoms;

Z is methylene;

$R_3$ and $R_4$ independent of each other represent hydrogen, alkyl having 1-10 C-atoms, alkenyl or alkynyl having 3-10 C-atoms, cycloalkyl having 3-8 ring atoms and 1-5 C-atoms in the alkyl group, or wherein $R_3 + R_4$ together with the nitrogen atom form alkyl substituted piperazine or piperidine;

$R_5$ is alkyl having 1-12 C-atoms, alkenyl or alkynyl having 3-12 C-atoms, cycloalkyl having 3-5 C-atoms, cycloalkyl-alkyl having 3-8 ring atoms and 1-5 C-atoms in the alkyl group, phenylalkyl having 1-5 C-atoms in the alkyl sub-group, phenylalkenyl or phenylalkynyl having 3-5 C-atoms in the alkenyl sub-group or alkynyl sub-group, which groups may be substituted with a group $(R_6)_p$, wherein $R_6$ is halogen, hydroxy, alkyl or hydroxyalkyl having 1-5 C-atoms, alkoxy having 1-3 C-atoms, S-alkyl, S(O)-alkyl or S(O)$_2$-alkyl having 1-3 C-atoms, amino, mono- or dialkylamino having 1-3 C-atoms per alkyl group, trifluoromethyl, trifluoromethoxy, a sulphonylamido group $SO_2NHR$ or a carbalkoxy group COOR wherein R is alkyl having 1-4 C-atoms, the group COOH, $SO_3H$, $CONH_2$, the amidino group or cyano group, and p has the value 0-3, and which alkyl sub-groups, alkenyl sub-groups and alkynyl sub-groups may contain a group —O—, —S— or CO,
or a pharmaceutically acceptable salt thereof.

5. A composition having anti-ischaemic, memory enhancing and anti-convulsive activity which comprises an anti-ischaemically, memory enhancingly and anti-convulsively effective amount of at least one compound as claimed in claim 4 as active component and a pharmaceutically acceptable carrier.

6. A method of treating ischaemia, impaired memory or epilepsy, comprising administering a compound according to claim 4 to a patient suffering from at least one of these diseases.

* * * * *